United States Patent [19]

Sommer et al.

[11] Patent Number: 5,015,635

[45] Date of Patent: May 14, 1991

[54] PESTICIDAL S-(HALOGENOALKYL)-DITHIOPHOSPHORIC(PHOSPHONIC) ACID ESTERS

[75] Inventors: Herbert Sommer, Remscheid; Jürgen Hartwig; Hans-Detlef Matthaei, both of Leverkusen, all of Fed. Rep. of Germany

[73] Assignee: Bayer Aktiengesellschaft, Leverkusen, Fed. Rep. of Germany

[21] Appl. No.: 385,850

[22] Filed: Jul. 26, 1989

[30] Foreign Application Priority Data

Aug. 4, 1988 [DE] Fed. Rep. of Germany ....... 3826449

[51] Int. Cl.[5] ..................... A01N 57/12; A01N 57/14; C07F 9/32; C07F 9/09

[52] U.S. Cl. .................................... 514/144; 514/129; 514/134; 514/135; 514/136; 514/130; 514/141; 558/186; 558/187; 558/188; 558/203; 558/204; 558/205; 558/206

[58] Field of Search ............... 558/203, 204, 186, 187, 558/188, 205, 206; 514/141, 144, 134, 135, 129, 130, 136

[56] References Cited

U.S. PATENT DOCUMENTS

| | | | |
|---|---|---|---|
| 3,093,536 | 6/1963 | Loeffler | 514/144 |
| 3,275,501 | 9/1966 | Schrader et al. | 514/144 |
| 3,896,219 | 7/1975 | Pianka | 514/144 |
| 4,104,377 | 8/1978 | Arlt et al. | 558/203 |
| 4,119,715 | 10/1978 | Hoffmann et al. | 558/203 |
| 4,678,778 | 7/1987 | Shortt et al. | 558/204 |

*Primary Examiner*—Mukund J. Shah
*Assistant Examiner*—E. Bernhardt

[57] ABSTRACT

Pesticidal S-(halogenoalkyl)-dithiophosphoric (phosphonic) acid esters of the formula

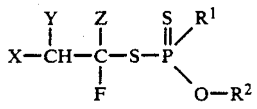

(I)

in which $R^1$ represents an optionally substituted radical from the group consisting of alkyl, alkenyl, alkoxy, alkenyloxy and alkinyloxy, $R^2$ represents an optionally substituted radical from the group consisting of alkyl, cycloalkyl, alkenyl, alkinyl and aryl, X and Y are identical or different and independently of one another represent hydrogen, halogen or alkyl, and Z represents hydrogen, halogen or alkyl.

16 Claims, No Drawings

PESTICIDAL S-(HALOGENOALKYL)-DITHIOPHOSPHORIC(-PHOSPHONIC) ACID ESTERS

The invention relates to new S-(halogenoalkyl)-dithiophosphoric(phosphonic) acid esters, a process for their preparation and their use as agents for combating pests, in particular as insecticides, acaricides and nematicides.

It is already known that certain thionophosphoric(-phosphonic) acid(amide) esters, such as, for example, 0-methyl0-(2-chloro-1-fluoro-ethyl)-thionophosphoric acid diesteramide and 0,0-diethyl-0-[1,2,2,2-tetrachloroethyl)-thionophosphoric acid ester, have a pesticidal action (compare DE-OS (German Published Specification) 2,629,016, corresponding to U.S. Pat. No. 4,159,324, and EP-OS 0,160,344). However, the action and the duration of the action of these known compounds is not always completely satisfactory, especially when low amounts are applied and in the case of low concentrations of active compound.

New S-(halogenoalkyl)-dithiophosphoric(phosphonic) acid esters of the general formula

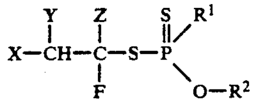

(I)

in which

- $R^1$ represents optionally substituted radicals from the series comprising alkyl, alkenyl, alkoxy, alkenyloxy and alkinyloxy (preferably alkoxy),
- $R^2$ represents optionally substituted radicals from the series comprising alkyl, cycloalkyl, alkenyl, alkinyl or aryl,
- X and Y are identical or different and independently of one another represent hydrogen, halogen or alkyl, and
- Z represents hydrogen, halogen or alkyl, have now been found.

The compounds of the formula (I) have at least one asymmetrically substituted carbon atom in the case where Z is other than fluorine and one asymmetrically substituted phosphorus atom. They can therefore exist in various optical isomer forms which can be obtained in various proportions. In all cases, they are predominantly in the form of racemates. The invention relates both to the isomer mixtures and to the individual isomers.

It has furthermore been found that the new S-(halogenoalkyl)-dithiophosphoric(phosphonic) acid esters of the formula (I) are obtained by a process in which dithiophosphoric(phosphonic) acids of the formula

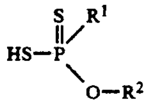

(II)

in which $R^1$ and $R^2$ have the abovementioned meanings, are reacted with fluoroalkenes of the formula

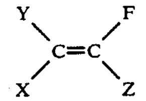

(III)

in which

X, Y and Z have the abovementioned meanings, if appropriate in the presence of a diluent.

The new S-(halogenoalkyl)-dithiophosphoric(phosphonic) acid esters of the formula (I) are surprisingly distinguished by a particularly high activity as agents for combating pests, in particular as insecticides, acaricides and nematicides.

The substances according to the invention thus represent a valuable enrichment of the art.

Optionally substituted alkyl in the definition of $R^1$ and $R^2$ and alkyl in the definition of X, Y and Z in the general formulae is represented by straight-chain or branched alkyl having preferably 1 to 20, particular preferably 1 to 12, especially 1 to 6 and especially particularly preferably 1 to 4 carbon atoms. Examples which may be mentioned are optionally substituted methyl, ethyl, n-propyl, i-propyl, n-butyl, sec.-butyl, i-butyl, tert-butyl, n-pentyl, i-pentyl and tert.-pentyl.

The term optionally substituted alkenyl itself or as a constituent of the alkenyloxy group in the definitions of $R^1$ and $R^2$ in the general formulae is represented by straight-chain or branched alkenyl having preferably 2 to 8, particularly preferably 2 to 6, in particular 2 to 4 and especially particularly preferably 3 carbon atoms. Examples which may be mentioned are optionally substituted vinyl, allyl, 2-butenyl, 3-butenyl and 1-methallyl.

The term optionally substituted alkoxy in the definition of $R^1$ in the general formulae is to be understood as being straight-chain or branched alkoxy having preferably 1 to 6, in particular 1 to 4, carbon atoms. Examples which may be mentioned are optionally substituted methoxy, ethoxy, propoxy, butoxy and their isomers, such as, for example, i-propoxy and i-, s- and tert.-butoxy, optionally substituted methoxy and ethoxy being mentioned as particularly preferred.

The term optionally substituted alkinyl itself or as a constituent of the alkinyloxy group in the definitions $R^1$ and $R^2$ in the general formulae is to be understood as being straight-chain or branched alkinyl having preferably 2 to 6, in particular 2 to 4 and particularly preferably 3 carbon atoms. Examples which may be mentioned are optionally substituted ethinyl, 2-propinyl, 2-butinyl, 3-butinyl and 1-methyl-2-propinyl.

Optionally substituted cycloalkyl in the definition $R^2$ is cycloalkyl having preferably 3 to 8, in particular 3, 5 or 6, carbon atoms.

Examples which may be mentioned are optionally substituted cyclopropyl, cyclobutyl, cyclopentyl, cyclohexyl and cycloheptyl.

The term optionally substituted aryl in the definition of $R^2$ in the general formulae is to be understood as meaning aryl having preferably 6 to 10 carbon atoms in the aryl part. Examples which may be mentioned are optionally substituted phenyl or naphthyl, in particular phenyl.

The substituted radicals mentioned in the definition of $R^1$ and $R^2$ can carry one or more, preferably 1 to 3 and in particular 1 or 2, identical or different substituents. Preferred substituents which may be mentioned for alkyl, alkenyl and alkinyl are: alkoxy having 1 to 4 carbon atoms, such as methoxy, ethoxy, n-propoxy, i-propoxy, n-butoxy, i-butoxy, sec.-butoxy and tert.-butoxy, and halogen (fluorine, chlorine, bromine and iodine, preferably fluorine, chlorine or bromine and in particular fluorine or chlorine).

The preferred substituents of the alkoxy, alkenyloxy and alkinyloxy radicals are halogens, such as fluorine, chlorine, bromine and iodine, in particular fluorine, chlorine and bromine, and/or alkoxy having preferably 1 to 4 carbon atoms, in particular methoxy or ethoxy.

Preferred substituents which may be mentioned for cycloalkyl and aryl are: alkyl having 1 to 4 carbon atoms, such as methyl, ethyl, n-propyl, i-propyl, n-butyl, i-butyl, sec.-butyl and tert.-butyl, halogenoalkyl having preferably 1 to 4, in particular 1 or 2, carbon atoms and preferably 1 to 5, in particular 1 to 3, halogen atoms (preferably fluorine, chlorine and/or bromine, in particular fluorine and/or chlorine, such as, for example, trifluoromethyl and halogen (preferably fluorine, chlorine and/or bromine, particularly preferably fluorine and/or chlorine and especially particularly preferably chlorine).

Other possible aryl substituents are also $C_1$–$C_4$-alkoxy, such as, for example, methoxy, ethoxy, n-propoxy, i-propoxy, n-butoxy, i-butoxy, sec.-butoxy and tert.-butoxy.

Halogen in the definitions X, Y and Z in the general formulae and as substituents of a group represents fluorine, chlorine, bromine and/or iodine, in particular fluorine, chlorine and/or bromine and particularly preferably in the case of X, Y and Z fluorine or chlorine.

In the general formulae, $R^1$ preferably represents alkyl or alkoxy which is optionally substituted by fluorine and/or chlorine and preferably has 1 to 6, in particular 1 to 4, carbon atoms.

In the general formulae, $R^2$ preferably represents alkyl which is optionally substituted by fluorine, chlorine or bromine or by $C_1$–$C_4$-alkoxy and preferably has 1 to 6, in particular 1 to 4, carbon atoms, or represents phenyl, which can be substituted by halogen (preferably chlorine).

The radicals $R^1$ and $R^2$ are preferably unsubstituted.

Y in the general formulae preferably represents hydrogen.

Z in the general formulae preferably represents fluorine.

Preferred S-(halogenoalkyl)-dithiophosphoric(phosphonic) acid esters of the formula (I) according to the invention are those in which $R^1$ represents $C_1$–$C_6$-alkyl and $C_2$–$C_4$-alkenyl which is optionally substituted by halogen or $C_1$–$C_4$-alkoxy; or represents $C_1$–$C_6$-alkoxy, $C_2$–$C_4$-alkenylalkoxy; and $C_2$–$C_4$-alkinyloxy which is optionally substituted by halogen and/or $C_1$–$C_4$-alkoxy (and preferably represents $C_1$–$C_4$-alkyl or $C_1$–$C_4$-alkoxy which is optionally substituted by halogen), $R^2$ represents $C_1$–$C_6$-alkyl which is optionally substituted by halogen and/or $C_1$–$C_4$-alkoxy; or represents cycloalkyl which is optionally substituted by $C_1$–$C_4$-alkyl and/or halogen and has 3 to 8 carbon atoms; or represents $C_2$–$C_4$-alkenyl and $C_2$–$C_4$-alkinyl which is optionally substituted by halogen, methyl and/or ethyl, or represents aryl which is optionally substituted by $C_1$–$C_4$-alkyl, $C_1$–$C_4$-alkoxy, $C_1$–$C_4$-halogenoalkyl having 1 to ]halogen atoms and/or halogen and has 6 to 10 carbon atoms (and preferably represents $C_1$–$C_6$-alkyl or phenyl which is optionally substituted by halogen), X and Y are identical or different and independently of one another represent hydrogen, fluorine, chlorine or bromine (preferably fluorine or chlorine) or $C_1$–$C_{20}$-alkyl (and preferably represent hydrogen) and Z represents hydrogen, fluorine, chlorine or $C_1$–$C_4$-alkyl (and preferably represents fluorine).

Particularly preferred S-(halogenoalkyl)-dithiophosphoric(phosphonic) acid esters of the formula (I) are those in which $R^1$ represents $C_1$–$C_2$-alkyl and $C_2$–$C_3$-alkenyl which is optionally substituted by fluorine, chlorine, methoxy and/or ethoxy; or represents $C_1$–$C_4$-alkoxy, $C_2$–$C_3$-alkenyloxy and $C_2$–$C_3$-alkinyloxy which is optionally substituted by fluorine, chlorine, methoxy and/or ethoxy (and preferably represents $C_1$–$C_4$-alkyl or $C_1$–$C_4$-alkoxy which is optionally substituted by halogen), $R^2$ represents $C_1$–$C_4$-alkyl which is optionally substituted by fluorine, chlorine, bromine, methoxy and/or ethoxy, or represents cycloalkyl which is optionally substituted by methyl, ethyl, fluorine and/or chlorine and has 3 to 6 carbon atoms; or represents $C_2$–$C_4$-alkenyl and $C_2$–$C_4$-alkinyl which is optionally substituted by fluorine and/or chlorine; or represents aryl which is optionally substituted by $C_1$–$C_2$-alkyl, $C_1$–$C_2$-alkoxy, $C_1$–$C_2$-halogenoalkyl having 1 to 3 halogen atoms or by fluorine, chlorine and/or bromine and has 6 to 10 carbon atoms (and preferably represents $C_1$–$C_4$-alkyl or phenyl which is optionally substituted by chlorine), X and Y are identical or different and independently of one another represent hydrogen, fluorine, chlorine and bromine (preferably fluorine or chlorine) or $C_1$–$C_{18}$-alkyl (and preferably represent hydrogen or $C_1$–$C_6$-alkyl in the case of X and hydrogen in the case of Y) and Z represents hydrogen, fluorine, chlorine or $C_1$–$C_2$-alkyl (preferably fluorine).

Examples which may be mentioned of the compounds of the general formula (I)

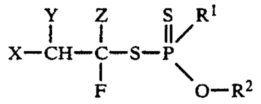

(I)

are:

TABLE 1

| X | Y | Z | $R^1$ | $R^2$ |
|---|---|---|---|---|
| H | H | H | $-OCH_3$ | $CH_3$ |
| H | H | H | $-OC_2H_5$ | $-C_3H_7$-i |
| H | H | H | $-OC_2H_5$ | $-C_4H_9$-i |
| H | H | H | $-OC_2H_5$ | $-C_4H_9$-s |
| H | H | H | $-CH_3$ | $-CH_3$ |
| H | H | H | $-CH_3$ | $-C_2H_5$ |
| H | H | H | $-C_2H_5$ | $-CH_3$ |
| H | H | H | $-C_2H_5$ | $-C_2H_5$ |
| H | H | F | $-C_2H_5$ | $-C_4H_9$-s |
| H | H | F | $-CH_3$ | $-CH_3$ |
| H | H | F | $-CH_3$ | $-C_2H_5$ |
| H | H | F | $-C_2H_5$ | $-CH_3$ |
| H | H | Cl | $-CH_3$ | $-CH_3$ |
| H | H | Cl | $-OC_2H_5$ | $-C_2H_5$ |
| H | H | Cl | $-OC_2H_5$ | $-C_3H_7$-i |
| H | H | Cl | $-OC_2H_5$ | $-C_4H_9$-i |
| H | H | Cl | $-OC_2H_5$ | $-C_4H_9$-s |
| H | H | Cl | $-CH_3$ | $-CH_3$ |

TABLE 1-continued

| X | Y | Z | $R^1$ | $R^2$ |
|---|---|---|---|---|
| H | H | Cl | —$CH_3$ | —$C_2H_5$ |
| H | H | Cl | —$C_2H_5$ | —$CH_3$ |
| H | H | Cl | —$C_2H_5$ | —$C_2H_5$ |
| H | H | —$CH_3$ | —$CH_3$ | —$CH_3$ |
| H | H | —$CH_3$ | —$OC_2H_5$ | —$C_2H_5$ |
| H | H | —$CH_3$ | —$OC_2H_5$ | —$C_3H_7$-i |
| H | H | —$CH_3$ | —$OC_2H_5$ | —$C_4H_9$-i |
| H | H | —$CH_3$ | —$OC_2H_5$ | —$C_4H_9$-s |
| H | H | —$CH_3$ | —$CH_3$ | —$CH_3$ |
| H | H | —$CH_3$ | —$CH_3$ | —$C_2H_5$ |
| H | H | —$CH_3$ | —$C_2H_5$ | —$CH_3$ |
| H | H | —$CH_3$ | —$C_2H_5$ | —$C_2H_5$ |
| H | H | H | —$CH_3$ | —$CH_3$ |
| H | F | H | —$OC_2H_5$ | —$C_2H_5$ |
| H | F | H | —$OC_2H_5$ | —$C_3H_7$-i |
| H | F | H | —$OC_2H_5$ | —$C_4H_9$-i |
| H | F | H | —$OC_2H_5$ | —$C_4H_9$-s |
| H | F | H | —$CH_3$ | —$CH_3$ |
| H | F | H | —$CH_3$ | —$C_2H_5$ |
| H | F | H | —$C_2H_5$ | —$CH_3$ |
| H | F | H | —$C_2H_5$ | —$C_2H_5$ |
| H | F | F | —$CH_3$ | —$CH_3$ |
| H | F | F | —$OC_2H_5$ | —$C_3H_7$-i |
| H | F | F | —$OC_2H_5$ | —$C_4H_9$-i |
| H | F | F | —$OC_2H_5$ | —$C_4H_9$-s |
| H | F | F | —$CH_3$ | —$CH_3$ |
| H | F | F | —$CH_3$ | —$C_2H_5$ |
| H | F | F | —$C_2H_5$ | —$CH_3$ |
| H | F | F | —$C_2H_5$ | —$C_2H_5$ |
| H | F | Cl | —$CH_3$ | —$CH_3$ |
| H | F | Cl | —$OC_2H_5$ | —$C_2H_5$ |
| H | F | Cl | —$OC_2H_5$ | —$C_3H_7$-i |
| H | F | Cl | —$OC_2H_5$ | —$C_4H_9$-i |
| H | F | Cl | —$OC_2H_5$ | —$C_4H_9$-s |
| H | F | Cl | —$CH_3$ | —$CH_3$ |
| H | F | Cl | —$CH_3$ | —$C_2H_5$ |
| H | F | Cl | —$C_2H_5$ | —$CH_3$ |
| H | F | Cl | —$C_2H_5$ | —$C_2H_5$ |
| H | F | $CH_3$ | —$CH_3$ | —$CH_3$ |
| H | F | $CH_3$ | —$OC_2H_5$ | —$C_2H_5$ |
| H | F | $CH_3$ | —$OC_2H_5$ | —$C_3H_7$-i |
| H | F | $CH_3$ | —$OC_2H_5$ | —$C_4H_9$-i |
| H | F | $CH_3$ | —$OC_2H_5$ | —$C_4H_9$-i |
| H | F | $CH_3$ | —$CH_3$ | —$CH_3$ |
| H | F | $CH_3$ | —$CH_3$ | —$C_2H_5$ |
| H | F | $CH_3$ | —$C_2H_5$ | —$CH_3$ |
| H | F | $CH_3$ | —$C_2H_5$ | —$C_2H_5$ |
| H | Cl | H | —$CH_3$ | —$CH_3$ |
| H | Cl | H | —$OC_2H_5$ | —$C_3H_7$-i |
| H | Cl | H | —$OC_2H_5$ | —$C_4H_9$-i |
| H | Cl | H | —$OC_2H_5$ | —$C_4H_9$-s |
| H | Cl | H | —$CH_3$ | —$CH_3$ |
| H | Cl | H | —$CH_3$ | —$C_2H_5$ |
| H | Cl | H | —$C_2H_5$ | —$CH_3$ |
| H | Cl | H | —$C_2H_5$ | —$C_2H_5$ |
| H | Cl | F | —$CH_3$ | —$CH_3$ |
| H | Cl | F | —$OC_2H_5$ | —$C_2H_5$ |
| H | Cl | F | —$OC_2H_5$ | —$C_3H_7$-i |
| H | Cl | F | —$OC_2H_5$ | —$C_4H_9$-i |
| H | Cl | F | —$OC_2H_5$ | —$C_4H_9$-s |
| H | Cl | F | —$CH_3$ | —$CH_3$ |
| H | Cl | F | —$CH_3$ | —$C_2H_5$ |
| H | Cl | F | —$C_2H_5$ | —$CH_3$ |
| H | Cl | F | —$C_2H_5$ | —$C_2H_5$ |
| H | Cl | Cl | —$CH_3$ | —$CH_3$ |
| H | Cl | Cl | —$OC_2H_5$ | —$C_2H_5$ |
| H | Cl | Cl | —$OC_2H_5$ | —$C_3H_7$-i |
| H | Cl | Cl | —$OC_2H_5$ | —$C_4H_9$-i |
| H | Cl | Cl | —$OC_2H_5$ | —$C_4H_9$-i |
| H | Cl | Cl | —$OC_2H_5$ | —$C_4H_9$-s |
| H | Cl | Cl | —$CH_3$ | —$CH_3$ |
| H | Cl | Cl | —$CH_3$ | —$C_2H_5$ |
| H | Cl | Cl | —$C_2H_5$ | —$CH_3$ |
| H | Cl | Cl | —$C_2H_5$ | —$C_2H_5$ |
| H | Cl | $CH_3$ | —$CH_3$ | —$CH_3$ |
| H | Cl | $CH_3$ | —$OC_2H_5$ | —$C_2H_5$ |
| H | Cl | $CH_3$ | —$OC_2H_5$ | —$C_3H_7$-i |
| H | Cl | $CH_3$ | —$OC_2H_5$ | —$C_4H_9$-i |
| H | Cl | $CH_3$ | —$OC_2H_5$ | —$C_4H_9$-s |
| H | Cl | $CH_3$ | —$CH_3$ | —$CH_3$ |
| H | Cl | $CH_3$ | —$CH_3$ | —$C_2H_5$ |

TABLE 1-continued

| X | Y | Z | $R^1$ | $R^2$ |
|---|---|---|---|---|
| H | Cl | $CH_3$ | —$C_2H_5$ | —$CH_3$ |
| H | Cl | $CH_3$ | —$C_2H_5$ | —$C_2H_5$ |
| H | $CH_3$ | H | —$CH_3$ | —$CH_3$ |
| H | $CH_3$ | H | —$OC_2H_5$ | —$C_2H_5$ |
| H | $CH_3$ | H | —$OC_2H_5$ | —$C_3H_7$-i |
| H | $CH_3$ | H | —$OC_2H_5$ | —$C_4H_9$-i |
| H | $CH_3$ | H | —$OC_2H_5$ | —$C_4H_9$-s |
| H | $CH_3$ | H | —$CH_3$ | —$CH_3$ |
| H | $CH_3$ | H | —$CH_3$ | —$C_2H_5$ |
| H | $CH_3$ | H | —$C_2H_5$ | —$CH_3$ |
| H | $CH_3$ | H | —$C_2H_5$ | —$C_2H_5$ |
| H | $CH_3$ | F | —$CH_3$ | —$CH_3$ |
| H | $CH_3$ | F | —$OC_2H_5$ | —$C_2H_5$ |
| H | $CH_3$ | F | —$OC_2H_5$ | —$C_3H_7$-i |
| H | $CH_3$ | F | —$OC_2H_5$ | —$C_4H_9$-i |
| H | $CH_3$ | F | —$OC_2H_5$ | —$C_4H_9$-s |
| H | $CH_3$ | F | —$CH_3$ | —$CH_3$ |
| H | $CH_3$ | F | —$CH_3$ | —$C_2H_5$ |
| H | $CH_3$ | F | —$C_2H_5$ | —$CH_3$ |
| H | $CH_3$ | F | —$C_2H_5$ | —$C_2H_5$ |
| H | $CH_3$ | Cl | —$CH_3$ | —$CH_3$ |
| H | $CH_3$ | Cl | —$OC_2H_5$ | —$C_2H_5$ |
| H | $CH_3$ | Cl | —$OC_2H_5$ | —$C_3H_7$-i |
| H | $CH_3$ | Cl | —$OC_2H_5$ | —$C_4H_9$-i |
| H | $CH_3$ | Cl | —$OC_2H_5$ | —$C_4H_9$-s |
| H | $CH_3$ | Cl | —$CH_3$ | —$CH_3$ |
| H | $CH_3$ | Cl | —$CH_3$ | —$C_2H_5$ |
| H | $CH_3$ | Cl | —$C_2H_5$ | —$CH_3$ |
| H | $CH_3$ | Cl | —$C_2H_5$ | —$C_2H_5$ |
| H | $CH_3$ | $CH_3$ | —$CH_3$ | —$CH_3$ |
| H | $CH_3$ | $CH_3$ | —$OC_2H_5$ | —$C_2H_5$ |
| H | $CH_3$ | $CH_3$ | —$OC_2H_5$ | —$C_3H_7$-i |
| H | $CH_3$ | $CH_3$ | —$OC_2H_5$ | —$C_4H_9$-i |
| H | $CH_3$ | $CH_3$ | —$OC_2H_5$ | —$C_4H_9$-s |
| H | $CH_3$ | $CH_3$ | —$CH_3$ | —$CH_3$ |
| H | $CH_3$ | $CH_3$ | —$CH_3$ | —$C_2H_5$ |
| H | $CH_3$ | $CH_3$ | —$C_2H_5$ | —$CH_3$ |
| H | $CH_3$ | $CH_3$ | —$C_2H_5$ | —$C_2H_5$ |
| F | F | H | —$CH_3$ | —$CH_3$ |
| F | F | H | —$OC_2H_5$ | —$C_2H_5$ |
| F | F | H | —$OC_2H_5$ | —$C_3H_7$-i |
| F | F | H | —$OC_2H_5$ | —$C_4H_9$-i |
| F | F | H | —$OC_2H_5$ | —$C_4H_9$-s |
| F | F | H | —$CH_3$ | —$CH_3$ |
| F | F | H | —$CH_3$ | —$C_2H_5$ |
| F | F | H | —$C_2H_5$ | —$CH_3$ |
| F | F | H | —$C_2H_5$ | —$C_2H_5$ |
| F | F | F | —$CH_3$ | —$CH_3$ |
| F | F | F | —$OC_2H_5$ | —$C_2H_5$ |
| F | F | F | —$OC_2H_5$ | —$C_3H_7$-i |
| F | F | F | —$OC_2H_5$ | —$C_4H_9$-i |
| F | F | F | —$OC_2H_5$ | —$C_4H_9$-s |
| F | F | F | —$CH_3$ | —$CH_3$ |
| F | F | F | —$CH_3$ | —$C_2H_5$ |
| F | F | F | —$C_2H_5$ | —$CH_3$ |
| F | F | F | —$C_2H_5$ | —$C_2H_5$ |
| F | F | Cl | —$CH_3$ | —$CH_3$ |
| F | F | Cl | —$OC_2H_5$ | —$C_2H_5$ |
| F | F | Cl | —$OC_2H_5$ | —$C_3H_7$-i |
| F | F | Cl | —$OC_2H_5$ | —$C_4H_9$-i |
| F | F | Cl | —$OC_2H_5$ | —$C_4H_9$-s |
| F | F | Cl | —$CH_3$ | —$CH_3$ |
| F | F | Cl | —$CH_3$ | —$C_2H_5$ |
| F | F | Cl | —$C_2H_5$ | —$CH_3$ |
| F | F | Cl | —$C_2H_5$ | —$C_2H_5$ |
| F | F | $CH_3$ | —$CH_3$ | —$CH_3$ |
| F | F | $CH_3$ | —$OC_2H_5$ | —$C_2H_5$ |
| F | F | $CH_3$ | —$OC_2H_5$ | —$C_3H_7$-i |
| F | F | $CH_3$ | —$OC_2H_5$ | —$C_4H_9$-i |
| F | F | $CH_3$ | —$OC_2H_5$ | —$C_4H_9$-s |
| F | F | $CH_3$ | —$CH_3$ | —$CH_3$ |
| F | F | $CH_3$ | —$CH_3$ | —$C_2H_5$ |
| F | F | $CH_3$ | —$C_2H_5$ | —$CH_3$ |
| F | F | $CH_3$ | —$C_2H_5$ | —$C_2H_5$ |
| F | Cl | H | —$CH_3$ | —$CH_3$ |
| F | Cl | H | —$OC_2H_5$ | —$C_2H_5$ |
| F | Cl | H | —$OC_2H_5$ | —$C_3H_7$-i |
| F | Cl | H | —$OC_2H_5$ | —$C_4H_9$-i |
| F | Cl | H | —$OC_2H_5$ | —$C_4H_9$-s |
| F | Cl | H | —$CH_3$ | —$CH_3$ |
| F | Cl | H | —$CH_3$ | —$C_2H_5$ |

TABLE 1-continued

| X | Y | Z | $R^1$ | $R^2$ |
|---|---|---|---|---|
| F | Cl | H | $-C_2H_5$ | $-CH_3$ |
| F | Cl | H | $-C_2H_5$ | $-C_2H_5$ |
| F | Cl | F | $-CH_3$ | $-CH_3$ |
| F | Cl | F | $-OC_2H_5$ | $-C_3H_7$-i |
| F | Cl | F | $-OC_2H_5$ | $-C_4H_9$-i |
| F | Cl | F | $-OC_2H_5$ | $-C_4H_9$-s |
| F | Cl | F | $-CH_3$ | $-CH_3$ |
| F | Cl | F | $-CH_3$ | $-C_2H_5$ |
| F | Cl | F | $-C_2H_5$ | $-CH_3$ |
| F | Cl | F | $-C_2H_5$ | $-C_2H_5$ |
| F | Cl | Cl | $-CH_3$ | $-CH_3$ |
| F | Cl | Cl | $-OC_2H_5$ | $-C_2H_5$ |
| F | Cl | Cl | $-OC_2H_5$ | $-C_3H_7$-i |
| F | Cl | Cl | $-OC_2H_5$ | $-C_4H_9$-i |
| F | Cl | Cl | $-OC_2H_5$ | $-C_4H_9$-s |
| F | Cl | Cl | $-CH_3$ | $-CH_3$ |
| F | Cl | Cl | $-CH_3$ | $-C_2H_5$ |
| F | Cl | Cl | $-C_2H_5$ | $-CH_3$ |
| F | Cl | Cl | $-C_2H_5$ | $-C_2H_5$ |
| F | Cl | $CH_3$ | $-CH_3$ | $-CH_3$ |
| F | Cl | $CH_3$ | $-OC_2H_5$ | $-C_2H_5$ |
| F | Cl | $CH_3$ | $-OC_2H_5$ | $-C_3H_7$-i |
| F | Cl | $CH_3$ | $-OC_2H_5$ | $-C_4H_9$-i |
| F | Cl | $CH_3$ | $-OC_2H_5$ | $-C_4H_9$-s |
| F | Cl | $CH_3$ | $-CH_3$ | $-CH_3$ |
| F | Cl | $CH_3$ | $-CH_3$ | $-C_2H_5$ |
| F | Cl | $CH_3$ | $-C_2H_5$ | $-CH_3$ |
| F | Cl | $CH_3$ | $-C_2H_5$ | $-C_2H_5$ |
| F | $CH_3$ | H | $-CH_3$ | $-CH_3$ |
| F | $CH_3$ | H | $-OC_2H_5$ | $-C_2H_5$ |
| F | $CH_3$ | H | $-OC_2H_5$ | $-C_3H_7$-i |
| F | $CH_3$ | H | $-OC_2H_5$ | $-C_4H_9$-i |
| F | $CH_3$ | H | $-OC_2H_5$ | $-C_4H_9$-s |
| F | $CH_3$ | H | $-CH_3$ | $-CH_3$ |
| F | $CH_3$ | H | $-CH_3$ | $-C_2H_5$ |
| F | $CH_3$ | H | $-C_2H_5$ | $-CH_3$ |
| F | $CH_3$ | H | $-C_2H_5$ | $-C_2H_5$ |
| F | $CH_3$ | F | $-CH_3$ | $-CH_3$ |
| F | $CH_3$ | F | $-OC_2H_5$ | $-C_2H_5$ |
| F | $CH_3$ | F | $-OC_2H_5$ | $-C_3H_7$-i |
| F | $CH_3$ | F | $-OC_2H_5$ | $-C_4H_9$-i |
| F | $CH_3$ | F | $-OC_2H_5$ | $-C_4H_9$-s |
| F | $CH_3$ | F | $-CH_3$ | $-CH_3$ |
| F | $CH_3$ | F | $-CH_3$ | $-C_2H_5$ |
| F | $CH_3$ | F | $-C_2H_5$ | $-CH_3$ |
| F | $CH_3$ | F | $-C_2H_5$ | $-C_2H_5$ |
| F | $CH_3$ | Cl | $-CH_3$ | $-CH_3$ |
| F | $CH_3$ | Cl | $-OC_2H_5$ | $-C_2H_5$ |
| F | $CH_3$ | Cl | $-OC_2H_5$ | $-C_3H_7$-i |
| F | $CH_3$ | Cl | $-OC_2H_5$ | $-C_4H_9$-i |
| F | $CH_3$ | Cl | $-OC_2H_5$ | $-C_4H_9$-s |
| F | $CH_3$ | Cl | $-CH_3$ | $-CH_3$ |
| F | $CH_3$ | Cl | $-CH_3$ | $-C_2H_5$ |
| F | $CH_3$ | Cl | $-C_2H_5$ | $-CH_3$ |
| F | $CH_3$ | Cl | $-C_2H_5$ | $-C_2H_5$ |
| F | $CH_3$ | $CH_3$ | $-CH_3$ | $-CH_3$ |
| F | $CH_3$ | $CH_3$ | $-OC_2H_5$ | $-C_2H_5$ |
| F | $CH_3$ | $CH_3$ | $-OC_2H_5$ | $-C_3H_7$-i |
| F | $CH_3$ | $CH_3$ | $-OC_2H_5$ | $-C_4H_9$-i |
| F | $CH_3$ | $CH_3$ | $-OC_2H_5$ | $-C_4H_9$-s |
| F | $CH_3$ | $CH_3$ | $-CH_3$ | $-CH_3$ |
| F | $CH_3$ | $CH_3$ | $-CH_3$ | $-C_2H_5$ |
| F | $CH_3$ | $CH_3$ | $-C_2H_5$ | $-CH_3$ |
| F | $CH_3$ | $CH_3$ | $-C_2H_5$ | $-C_2H_5$ |
| Cl | Cl | H | $-CH_3$ | $-CH_3$ |
| Cl | Cl | H | $-OC_2H_5$ | $-C_2H_5$ |
| Cl | Cl | H | $-OC_2H_5$ | $-C_3H_7$-i |
| Cl | Cl | H | $-OC_2H_5$ | $-C_4H_9$-i |
| Cl | Cl | H | $-OC_2H_5$ | $-C_4H_9$-s |
| Cl | Cl | H | $-CH_3$ | $-CH_3$ |
| Cl | Cl | H | $-CH_3$ | $-C_2H_5$ |
| Cl | Cl | H | $-C_2H_5$ | $-CH_3$ |
| Cl | Cl | H | $-C_2H_5$ | $-C_2H_5$ |
| Cl | Cl | F | $-CH_3$ | $-CH_3$ |
| Cl | Cl | F | $-OC_2H_5$ | $-C_2H_5$ |
| Cl | Cl | F | $-OC_2H_5$ | $-C_3H_7$-i |
| Cl | Cl | F | $-OC_2H_5$ | $-C_4H_9$-i |
| Cl | Cl | F | $-OC_2H_5$ | $-C_4H_9$-s |
| Cl | Cl | F | $-CH_3$ | $-CH_3$ |
| Cl | Cl | F | $-CH_3$ | $-C_2H_5$ |
| Cl | Cl | F | $-C_2H_5$ | $-CH_3$ |

TABLE 1-continued

| X | Y | Z | $R^1$ | $R^2$ |
|---|---|---|---|---|
| Cl | Cl | F | $-C_2H_5$ | $-C_2H_5$ |
| Cl | Cl | Cl | $-CH_3$ | $-CH_3$ |
| Cl | Cl | Cl | $-OC_2H_5$ | $-C_2H_5$ |
| Cl | Cl | Cl | $-OC_2H_5$ | $-C_3H_7$-i |
| Cl | Cl | Cl | $-OC_2H_5$ | $-C_4H_9$-i |
| Cl | Cl | Cl | $-OC_2H_5$ | $-C_4H_9$-s |
| Cl | Cl | Cl | $-CH_3$ | $-CH_3$ |
| Cl | Cl | Cl | $-CH_3$ | $-C_2H_5$ |
| Cl | Cl | Cl | $-C_2H_5$ | $-CH_3$ |
| Cl | Cl | Cl | $-C_2H_5$ | $-C_2H_5$ |
| Cl | Cl | $CH_3$ | $-CH_3$ | $-CH_3$ |
| Cl | Cl | $CH_3$ | $-OC_2H_5$ | $-C_2H_5$ |
| Cl | Cl | $CH_3$ | $-OC_2H_5$ | $-C_3H_7$-i |
| Cl | Cl | $CH_3$ | $-OC_2H_5$ | $-C_4H_9$-i |
| Cl | Cl | $CH_3$ | $-OC_2H_5$ | $-C_4H_9$-s |
| Cl | Cl | $CH_3$ | $-CH_3$ | $-CH_3$ |
| Cl | Cl | $CH_3$ | $-CH_3$ | $-C_2H_5$ |
| Cl | Cl | $CH_3$ | $-C_2H_5$ | $-CH_3$ |
| Cl | Cl | $CH_3$ | $-C_2H_5$ | $-C_2H_5$ |
| Cl | $CH_3$ | H | $-CH_3$ | $-CH_3$ |
| Cl | $CH_3$ | H | $-OC_2H_5$ | $-C_2H_5$ |
| Cl | $CH_3$ | H | $-OC_2H_5$ | $-C_3H_7$-i |
| Cl | $CH_3$ | H | $-OC_2H_5$ | $-C_4H_9$-i |
| Cl | $CH_3$ | H | $-OC_2H_5$ | $-C_4H_9$-s |
| Cl | $CH_3$ | H | $-CH_3$ | $-CH_3$ |
| Cl | $CH_3$ | H | $-CH_3$ | $-C_2H_5$ |
| Cl | $CH_3$ | H | $-C_2H_5$ | $-CH_3$ |
| Cl | $CH_3$ | H | $-C_2H_5$ | $-C_2H_5$ |
| Cl | $CH_3$ | F | $-CH_3$ | $-CH_3$ |
| Cl | $CH_3$ | F | $-OC_2H_5$ | $-C_2H_5$ |
| Cl | $CH_3$ | F | $-OC_2H_5$ | $-C_3H_7$-i |
| Cl | $CH_3$ | F | $-OC_2H_5$ | $-C_4H_9$-i |
| Cl | $CH_3$ | F | $-OC_2H_5$ | $-C_4H_9$-s |
| Cl | $CH_3$ | F | $-CH_3$ | $-CH_3$ |
| Cl | $CH_3$ | F | $-CH_3$ | $-C_2H_5$ |
| Cl | $CH_3$ | F | $-C_2H_5$ | $-CH_3$ |
| Cl | $CH_3$ | F | $-C_2H_5$ | $-C_2H_5$ |
| Cl | $CH_3$ | Cl | $-CH_3$ | $-CH_3$ |
| Cl | $CH_3$ | Cl | $-OC_2H_5$ | $-C_2H_5$ |
| Cl | $CH_3$ | Cl | $-OC_2H_5$ | $-C_3H_7$-i |
| Cl | $CH_3$ | Cl | $-OC_2H_5$ | $-C_4H_9$-i |
| Cl | $CH_3$ | Cl | $-OC_2H_5$ | $-C_4H_9$-s |
| Cl | $CH_3$ | Cl | $-CH_3$ | $-CH_3$ |
| Cl | $CH_3$ | Cl | $-CH_3$ | $-C_2H_5$ |
| Cl | $CH_3$ | Cl | $-C_2H_5$ | $-CH_3$ |
| Cl | $CH_3$ | Cl | $-C_2H_5$ | $-C_2H_5$ |
| Cl | $CH_3$ | $CH_3$ | $-CH_3$ | $-CH_3$ |
| Cl | $CH_3$ | $CH_3$ | $-OC_2H_5$ | $-C_2H_5$ |
| Cl | $CH_3$ | $CH_3$ | $-OC_2H_5$ | $-C_3H_7$-i |
| Cl | $CH_3$ | $CH_3$ | $-OC_2H_5$ | $-C_4H_9$-i |
| Cl | $CH_3$ | $CH_3$ | $-OC_2H_5$ | $-C_4H_9$-s |
| Cl | $CH_3$ | $CH_3$ | $-CH_3$ | $-CH_3$ |
| Cl | $CH_3$ | $CH_3$ | $-CH_3$ | $-C_2H_5$ |
| Cl | $CH_3$ | $CH_3$ | $-C_2H_5$ | $-CH_3$ |
| Cl | $CH_3$ | $CH_3$ | $-C_2H_5$ | $-C_2H_5$ |
| $CH_3$ | $CH_3$ | H | $-CH_3$ | $-CH_3$ |
| $CH_3$ | $CH_3$ | H | $-OC_2H_5$ | $-C_2H_5$ |
| $CH_3$ | $CH_3$ | H | $-OC_2H_5$ | $-C_3H_7$-i |
| $CH_3$ | $CH_3$ | H | $-OC_2H_5$ | $-C_4H_9$-i |
| $CH_3$ | $CH_3$ | H | $-OC_2H_5$ | $-C_4H_9$-s |
| $CH_3$ | $CH_3$ | H | $-CH_3$ | $-CH_3$ |
| $CH_3$ | $CH_3$ | H | $-CH_3$ | $-C_2H_5$ |
| $CH_3$ | $CH_3$ | H | $-C_2H_5$ | $-CH_3$ |
| $CH_3$ | $CH_3$ | H | $-C_2H_5$ | $-C_2H_5$ |
| $CH_3$ | $CH_3$ | F | $-CH_3$ | $-CH_3$ |
| $CH_3$ | $CH_3$ | F | $-OC_2H_5$ | $-C_2H_5$ |
| $CH_3$ | $CH_3$ | F | $-OC_2H_5$ | $-C_3H_7$-i |
| $CH_3$ | $CH_3$ | F | $-OC_2H_5$ | $-C_4H_9$-i |
| $CH_3$ | $CH_3$ | F | $-OC_2H_5$ | $-C_4H_9$-s |
| $CH_3$ | $CH_3$ | F | $-CH_3$ | $-CH_3$ |
| $CH_3$ | $CH_3$ | F | $-CH_3$ | $-C_2H_5$ |
| $CH_3$ | $CH_3$ | F | $-C_2H_5$ | $-CH_3$ |
| $CH_3$ | $CH_3$ | F | $-C_2H_5$ | $-C_2H_5$ |
| $CH_3$ | $CH_3$ | Cl | $-CH_3$ | $-CH_3$ |
| $CH_3$ | $CH_3$ | Cl | $-OC_2H_5$ | $-C_2H_5$ |
| $CH_3$ | $CH_3$ | Cl | $-OC_2H_5$ | $-C_3H_7$-i |
| $CH_3$ | $CH_3$ | Cl | $-OC_2H_5$ | $-C_4H_9$-i |
| $CH_3$ | $CH_3$ | Cl | $-OC_2H_5$ | $-C_4H_9$-s |
| $CH_3$ | $CH_3$ | Cl | $-CH_3$ | $-CH_3$ |
| $CH_3$ | $CH_3$ | Cl | $-CH_3$ | $-C_2H_5$ |
| $CH_3$ | $CH_3$ | Cl | $-C_2H_5$ | $-CH_3$ |

TABLE 1-continued

| X | Y | Z | $R^1$ | $R^2$ |
|---|---|---|---|---|
| $CH_3$ | $CH_3$ | Cl | $-C_2H_5$ | $-C_2H_5$ |
| $CH_3$ | $CH_3$ | $CH_3$ | $-CH_3$ | $-CH_3$ |
| $CH_3$ | $CH_3$ | $CH_3$ | $-OC_2H_5$ | $-C_2H_5$ |
| $CH_3$ | $CH_3$ | $CH_3$ | $-OC_2H_5$ | $-C_3H_7$-i |
| $CH_3$ | $CH_3$ | $CH_3$ | $-OC_2H_5$ | $-C_4H_9$-i |
| $CH_3$ | $CH_3$ | $CH_3$ | $-OC_2H_5$ | $-C_4H_9$-s |
| $CH_3$ | $CH_3$ | $CH_3$ | $-CH_3$ | $-CH_3$ |
| $CH_3$ | $CH_3$ | $CH_3$ | $-CH_3$ | $-C_2H_5$ |
| $CH_3$ | $CH_3$ | $CH_3$ | $-C_2H_5$ | $-CH_3$ |
| $CH_3$ | $CH_3$ | $CH_3$ | $-C_2H_5$ | $-C_2H_5$ |

Especially particularly preferred S-(halogenoalkyl)-dithiophosphoric(phosphonic) acid esters of the formula (I) are those in which $R^1$ represents ($C_1$–$C_4$)-alkyl, $C_1$–$C_4$-alkoxy or ($C_2$–$C_3$)-alkenyloxy which is optionally substituted by fluorine, chlorine and/or methoxy (and preferably represents $C_1$–$C_4$-alkyl or $C_1$–$C_4$-alkoxy), $R^2$ represents $C_1$–$C_4$-alkyl which is optionally substituted by fluorine, chlorine, bromine and/or methoxy, or represents cycloalkyl having 3 to 6 carbon atoms; or represents $C_2$–$C_4$-alkenyl or $C_2$–$C_4$-alkinyl or represents phenyl which is optionally substituted by $C_1$–$C_2$-alkyl, $C_1$–$C_2$-alkoxy, $C_1$–$C_2$-halogenoalkyl having 1 to 3 halogen atoms or by fluorine, chlorine and/or bromine (and preferably represents $C_1$–$C_4$-alkyl), X and Y are identical or different and independently of one another represent hydrogen, fluorine, chlorine or ($C_1$–$C_{16}$)-alkyl (and preferably represent hydrogen) and Z represents hydrogen, fluorine, chlorine or methyl (and preferably represents fluorine).

S-(Halogenoalkyl)-dithiophosphoric(phosphonic) acid esters of the formula (I) which are especially particularly singled out are those in which $R^1$ represents methyl, ethyl, methoxy, ethoxy, propoxy or butoxy, $R^2$ represents methyl, ethyl or propyl, or represents phenyl which is optionally substituted by methyl, methoxy, trifluoromethyl, fluorine and chlorine, X and Y are identical or different and independently of one another represent hydrogen, fluorine, chlorine, methyl, ethyl, propyl, butyl or ethyl-pentyl and Z represents hydrogen and fluorine.

If, for example, 0,0-diethyl-dethiophosphoric acid and vinylidene fluoride are used as starting substances, the course of the reaction in the process according to the invention can be represented by the following equation:

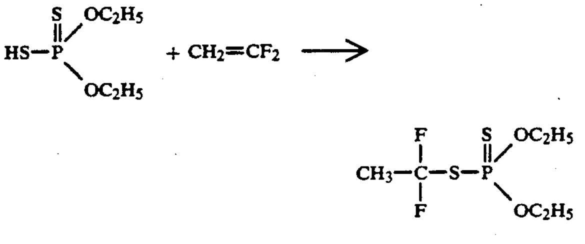

Formula (II) provides a general definition of the dithiophosphoric(phosphonic) acids to be used as starting substances in the process according to the invention. In this formula (II), $R^1$ and $R^2$ preferably or particularly preferably represent those radicals which are mentioned above in the definitions for formula (I).

The di-thiophosphoric(phosphonic) acids of the formula (II) are generally known compounds of organic chemistry.

Formula (III) provides a general definition of the fluoroalkenes also to be used as starting substances in the process according to the invention. In this formula (III), X, Y and Z preferably or particularly preferably represent those radicals which are mentioned above in the definition for formula (I).

The fluoroalkenes of the formula (III) are generally known compounds of organic chemistry or can be obtained according to known methods.

If appropriate, the process according to the invention for the preparation of the new compounds of the formula (I) is carried out using diluents.

These include, in particular, aliphatic or aromatic, optionally halogenated hydrocarbons, such as, for example, pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylenesulphone and hexamethylphosphoric acid triamide.

The reaction temperatures can be varied within a substantial range in the process for the preparation of the compounds of the formula (I). The reaction is in general carried out at temperatures between 0° C. and 200° C., preferably at temperatures between 80° C. and 140° C.

The reaction can in general be allowed to proceed under increased pressure. The reaction participants are preferably employed in an equimolar ratio for carrying out the process according to the invention. An excess of one or the other of the components in general provides no substantial advantages. However, it may be advantageous to employ the compounds of the formula (III) in excess (preferably in an amount of 1.5 to 4 mols per mol of starting substance of the formula (II). If appropriate, the reaction is carried out in one of the solvents mentioned. The batch is worked up by customary methods, by washing the reaction mixture with dilute aqueous bases, separating off the organic phase and distilling off the solvents.

The new compounds are obtained in the form of oils, some of which cannot be distilled without decomposition but can be freed from the last volatile constituents by so-called "incipient distillation", that is to say by prolonged heating at a moderately elevated temperature under reduced pressure, and can be purified in this way. They are characterized by their retention index (Kovats index).

The active compounds are suitable for combating animal pests, preferably arthropods and nematodes, in particular insects and arachnida, encountered in agriculture, in forestry, in the protection of stored products and of materials, and in the hygiene field. They are active against normally sensitive and resistant species and against all or some stages of development. The abovementioned pests include:

From the order of the Isopoda, for example, Oniscus asellus, Armadillidium vulgare and Porcellio scaber. From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.* From the order of the Dermaptera, for example, *Forficula auricularia.* From the order of the Isoptera, for example, *Reticulitermes* spp.. From the order of the Anoplura, for example, *Phylloxera vastatrix, Pemphigus* spp., *Pediculus humanus corporis, Haematopinus* spp. and *Linognathus* spp. From the order of the Mallophaga, for example, *Trichodectes* spp. and *Damalinea* spp. From the order of the Thysanoptera, for example, *Hercinothrips femoralis* and *Thrips tabaci.* From the order of the Heteroptera, for example, *Eurygaster* spp., *Dysdercus intermedius, Piesma quadrata, Cimex lectularius, Rhodnius prolixus* and *Triatoma* spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi, Empoasca* spp , *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euprocpadella, chrysorrhoea, Lymantria* spp. *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., Trichoplusia ni, Carpocapsa pomonella, Pieris spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varive stis, Atomaria* spp., *Oryzaephilus surinamensis, Antho nomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp. *Niptus hololeucus, Gibbium psylloides, Tribolium* spp., *Tenebrio molitor, Agriotes* spp., *Conoderus* spp., Melolontha melolontha, Amphimallon solstitialis and *Costelytra zealandica.* From the order of the Hymenoptera, for example, *Diprion* spp., *Hoplocampa* spp., *Lasius* spp., *Monomorium pharaomis* and *Vespa* spp. From the order of the Diptera, for example, *Aedes* spp., *Anopheles spp., Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio* hortulanus, *Oscinella* frit, *Phorbia* spp., *Pegomyia hyoscyami, Ceratitis capitata, Dacus oleae* and *Tipula paludosa.* From the order of the Siphonaptera, for example, *Xenopsylla cheopis* and *Ceratophyllus* spp. From the order of the Arachnida, for example, *Scorpio maurus* and *Latrodectus mactans.* From the order of the Acarina, example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp, *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The phytoparasitic nematodes include *Pratylenchus* spp., *Radopholus similis, Ditylenchus dipsaci, Tylenchulus* semi-penetrans, *Heterodera* spp., *Meloidogyne* spp., *Aphelenchoides* spp., *Longidorus* spp., *Xiphinema* spp. and *Trichodorus* spp..

The active compounds of the formula (I) according to the invention are distinguished by an outstanding insecticidal activity. When used as soil insecticides in particular, they exhibit an outstanding action against grubs, such as, for example, Porbia antiqua maggots and Diabrotica balteata larvae.

The active compounds according to the invention are also distinguished by an outstanding insecticidal activity, especially in combating Coleoptera species, such as, for example, Sitophilus granarius, and are also particularly suitable for combating hygiene pests and pests of stored products, such as, for example, Aedes aegypti larvae. Some of the active compounds according to the invention also exhibit an action as a leaf fungicide and a fungicidal action against Pyricularia oryzae on rice.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produces in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES:

EXAMPLE 1

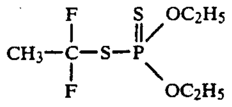

110 g (0.39 mol) of 0,0-diethyldithiophosphoric acid and 100 g (1.56 mol) of vinylidene fluoride are heated at 110° C. in an autoclave under 80 bar for 6.5 hours. The reaction mixture is taken up in toluene and washed with dilute sodium hydroxide solution, the organic phase is separated off and dried over magnesium sulphate, the toluene is evaporated off and the residue is distilled under greatly reduced pressure. 84.2 g (57% of theory) of 0,0-diethyl-S-(1,1-difluoro-ethyl)-di-thiophosphoric acid triester of boiling point 61° C./0.15 mbar and retention index 1244* are obtained.

* The retention indices (Kovats index) were determined by gas chromatography on a boiling point phase (dimethylsilicone).

The end products of the formula

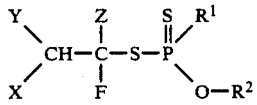

(I)

Listed in the following Table 2 are obtained in an analogous manner to Example (1), taking into consideration the information in the description on the process according to the invention:

TABLE 2

| Example No. | X | Y | Z | $R^1$ | $R^2$ | Retention index* |
|---|---|---|---|---|---|---|
| 2 | H | H | F | $O-C_3H_7$-i | $C_3H_7$-i | 1314 |
| 3 | H | H | F | $C_2H_5$ | $C_4H_9$-i | 1384 |
| 4 | $C_{14}H_{29}$ | H | F | $O-C_3H_7$-i | $C_3H_7$-i | |
| 5 | $CH-C_4H_9$<br>$C_2H_5$ | H | F | $O-C_2H_5$ | $C_2H_5$ | 1846 |
| 6 | H | H | F | $O-C_2H_5$ | $C_4H_9$-i | 1375 |
| 7 | H | H | F | $O-C_4H_9$-i | $C_4H_9$-i | 1499 |
| 8 | H | H | F | $C_2H_5$ | 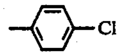 | 1861 |
| 9 | H | H | F | $O-C_2H_5$ | $C_3H_7$-i | 1282 |
| 10 | H | H | F | $O-CH_3$ | $CH_3$ | 1133 |
| 11 | H | H | F | $C_2H_5$ | $C_2H_5$ | 1249 |
| 12 | H | H | H | $O-C_2H_5$ | $C_2H_5$ | 1289 |
| 13 | Cl | F | F | $O-C_2H_5$ | $C_2H_5$ | 1360 |
| 14 | H | Cl | H | $O-C_2H_5$ | $C_2H_5$ | |
| 15 | H | F | F | $O-C_2H_5$ | $C_2H_5$ | |

*The retention indices (Kovats index) were determined by gas chromatography on a boiling point phase (dimethylsilicone).

USE EXAMPLES

The compounds shown below were employed as comparison compounds in the use examples which follow:

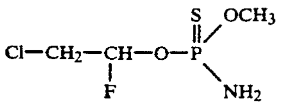

(A)

(known from DE-OS (German Published Specification) 2,629,016, which corresponds to U.S. Pat. No. 4,159,324).

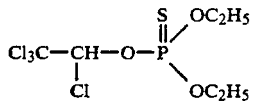

(B)

(known from EP-OS 0,160,344)

EXAMPLE A

Test insect: Phorbia antiqua maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/1), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Examples 1, 2, 3, 5, 6, 7, 8, 9, 11 and 12 at a concentration of, for example, 20 ppm showed a degree of effectiveness of 100%, whereas comparison compound A at the same concentration gave a degree of effectiveness of 0%.

EXAMPLE B

Test insect: Diabrotica balteata larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance here, only the amount by weight of active compound per unit volume of soil, which is given in ppm (=mg/1), being decisive. The soil is filled into pots and the pots are left to stand at room temperature.

Immediately after the preparation, 6 pregerminated corn seeds are placed in each pot. After 2 days, the corresponding test insects are placed in the treated soil.

After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Example 1 at a concentration of, for example, 0.3 ppm showed a degree of destruction of 95%, whereas comparison compound (B) at the same concentration gave no destruction (0%).

EXAMPLE C

Mosquito larvae test

Test insects: Aedes aegypti larvae
Solvent: 99 parts by weight of acetone
Emulsifier: 1 part by weight of benzylhydroxybiphenylpolyglycol ether.

To produce a suitable preparation of active compound, 2 parts by weight of active compound are dissolved in 1,000 parts by volume of the solvent, containing the amount of emulsifier stated above. The solution thus obtained is diluted with water to the desired lower concentrations.

The aqueous preparations of active compound of the desired concentration are filled into glass vessels and about 25 mosquito larvae are then placed in each glass vessel.

After 24 hours, the degree of destruction in % is determined. 100% means that all larvae have been killed. 0% means that no larvae at all have been killed.

In this test, for example, the compound of Preparation Example 3 at a a concentration of, for example, 0.1 ppm showed a degree of destruction of 100%, whereas comparison compound (A) at a concentration of 1 ppm gave no destruction (0%).

EXAMPLE D

Test insects: Sitophelia granarius
Solvent: acetone 2 parts by weight of active compound are taken up in 1,000 parts by volume of solvent. The solution thus obtained is diluted with further solvent to the desired concentration.

2.5 ml of the active compound solution are pipetted into a Petri dish. A filterpaper disc of about 9.5 cm diameter is located on the bottom of the Petri dish. The Petri dish is left standing open until the solvent has completely evaporated. The amount of active compound per $m^2$ of filterpaper varies, depending on the concentration of the active compound solution. The stated number of test insects is then introduced into the Petri dish, and the dish is covered with a glass lid.

The condition of the test insects is checked 3 days after the experiments have been set up. The destruction in % is determined. 100% means that all the test insects have been killed; 0% means that none of the test insects have been killed.

In this test, for example, the compound of Preparation Example 3 at a concentration of, for example, 0.002% showed destructions of 100%, whereas comparison compound (A) at the same concentration gave a destruction of 30%.

It is understood that the specification and examples are illustrative but not limitative of the present invention and that other embodiments within the spirit and scope of the invention will suggest themselves to those skilled in the art.

We claim:

1. An S-(halogenoalkyl)-dithiophosphoric acid ester of the formula

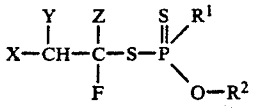

(I)

in which $R^1$ represents $C_1$–$C_6$-alkoxy, $C_2$–$C_4$-alkenyloxy or $C_2$–$C_4$-alkynyloxy which is optionally substituted by a member selected from the group consisting of halogen and $C_1$–$C_4$-alkoxy, $R^2$ represents $C_1$–$C_6$-alkyl which is optionally substituted by a member selected from the group consisting of halogen and $C_1$–$C_4$-alkoxy; or represents cycloalkyl which has 3 to 8 carbon atoms and is optionally substituted by a member selected from the group consisting of $C_1$–$C_4$-alkyl and halogen; or represents $C_2$–$C_4$-alkenyl or $C_2$–$C_4$ alkynyl which is optionally substituted by a member selected from the group consisting of halogen, methyl and ethyl, or represents aryl which has 6 to 10 carbon atoms and which is optionally substituted by a member selected from the group consisting of $C_1$–$C_4$-alkyl, $C_1$–$C_4$-alkoxy, $C_1$–$C_4$-halogenoalkyl having 1 to 9 halogen atoms and halogen, X and Y are identical or different and independently of one another represent hydrogen, fluorine, chlorine, bromine or $C_1$–$C_{20}$-alkyl and Z represents hydrogen, fluorine, chlorine or $C_1$–$C_4$-alkyl.

2. An S-(halogenoalkyl)-dithiophosphoric acid ester according to claim 1, in which $R^1$ represents $C_1$–$C_4$-alkoxy, $C_2$–$C_3$-alkenyloxy and $C_2$–$C_3$-alkynyloxy which is optionally substituted by a member selected from the group consisting of fluorine, chlorine, methoxy and ethoxy, $R^2$ represents $C_1$–$C_4$-alkyl which is optionally substituted by a member selected from the group consisting of fluorine, chlorine, bromine, methoxy and ethoxy, or represents cycloalkyl which has 3 to 6 carbon atoms and is optionally substituted by a member selected from group consisting of methyl, ethyl, fluorine and chlorine; or represents $C_2$–$C_4$-alkenyl or $C_2$–$C_4$ alkynyl which is optionally substituted by a member selected from group consisting of fluorine and chlorine; or represents aryl which has 6 to 10 carbon atoms and is optionally substituted by a member selected from group consisting of $C_1$–$C_2$-alkyl, $C_1$–$C_2$-alkoxy, $C_1$–$C_2$-halogenoalkyl having 1 to 3 halogen atoms, fluorine, chlorine and bromine, X and Y are identical or different and independently of one another represent hydrogen, fluorine, chlorine, bromine or $C_1$–$C_{18}$-alkyl and Z represents hydrogen, fluorine, chlorine or $C_1$–$C_2$-alkyl.

3. A compound according to claim 1 in which

X and Y represent hydrogen.

4. A compound according to claim 1 in which

Z represents fluorine.

5. A compound according to claim 1, wherein such compound is 0,0-diethyl-S-(1,1-difluoro-ethyl)-dithiophosphoric acid triester of the formula

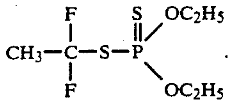

6. A compound according to claim 1, wherein such compound is 0,0-diisopropyl-S-(1,1-difluoro-ethyl)-dithiophosphoric acid triester of the formula

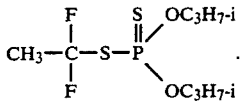

7. A compound according to claim 1, wherein such compound is 0-ethyl-0-isobutyl-S-(1,1-difluoro-ethyl)-dithiophosphoric acid triester of the formula

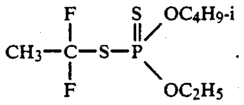

8. A compound according to claim 1, wherein such compound is 0-ethyl-0-isopropyl-S-(1,1-difluoro-ethyl)-dithiophosphoric acid triester of the formula

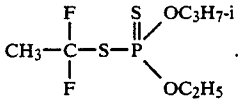

9. A compound according to claim 1, in which $R^1$ represents $C_1$–$C_6$-alkoxy, and $R^2$ represents $C_1$–$C_6$-alkyl.

10. An insecticidal, acaricidal or nematicidal composition comprising an insecticidally, acaricidally or nematicidally effective amount of a compound according to claim 1 and a diluent.

11. A method of combating insects, acarids or nematodes which comprises applying to such insects, acarids or nematodes or to an insect, acarid or namatode habitat an insecticidally, acaricidally or nematicidally effective amount of a compound according to claim 1.

12. The method according to claim 11, wherein such compound is 0,0-diethyl-S-(1,1-difluoro-ethyl)-dithiophosphoric acid triester, 0,0-diisopropyl-S-(1,1-difluoro-ethyl)-dithiophosphoric acid triester, 0-ethyl-0-isobutyl-S-(1,1-difluoro-ethyl)-dithiophosphoric acid triester, or 0-ethyl-0-isopropyl-S-(1,1-difluoro-ethyl)-dithiophosphoric acid triester.

13. An S-(halogenoalkyl)-dithio-phosphonic acid ester of the formula

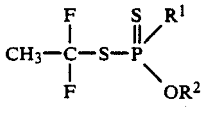

in which $R^1$ represents $C_1$–$C_6$-alkyl or $C_2$–$C_4$-alkenyl which is optionally substituted by halogen or $C_1$–$C_4$-alkyl which is $R^2$ represents $C_1$–$C_6$-alkyl which is optionally substituted by a member selected from the group consisting of halogen and $C_1$–$C_4$-alkoxy; or represents cycloalkyl which has 3 to 8 carbon atoms and is optionally substituted by a member selected from the group consisting of $C_1$–$C_4$-alkyl and halogen; or represents $C_2$–$C_4$-alkenyl or $C_2$–$C_4$-alkynyl which is optionally substituted by a member selected from the group consisting of halogen, methyl and ethyl, or represents aryl which has 6 to 10 carbon atoms and which is optionally substituted by a member selected from the group consisting of $C_1$–$C_4$-alkyl, $C_1$–$C_4$-alkoxy, $C_1$–$C_4$-halogenoalkyl having 1 to 9 halogen atoms and halogen.

14. A compound according to claim 13, wherein such compound is 0-ethyl-S-(1,1-difluoro-ethyl)-ethanedithiophosphonic acid diester of the formula

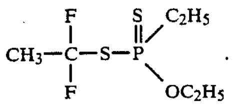

15. An insecticidal, acaricidal or nematicidal composition comprising an insecticidally, acaricidally or nematicidally effective amount of a compound according to claim 13 and a diluent.

16. A method of combating insects, acarids or nematodes which comprises applying to such insects, acarids or nematodes or to an insect, acarid, or nematode habitat an insecticidally, acaricidally or namaticidally effective amount of a compound according to claim 13.

* * * * *